United States Patent

Stanley et al.

[11] Patent Number: 5,824,334
[45] Date of Patent: *Oct. 20, 1998

[54] TOBACCO SUBSTITUTE

[75] Inventors: Theodore H. Stanley, Salt Lake City; Brian I. Hague, West Valley City, both of Utah

[73] Assignee: University of Utah Research Foundation, Salt Lake City, Utah

[*] Notice: The term of this patent shall not extend beyond the expiration date of Pat. No. 5,288,497.

[21] Appl. No.: 636,828

[22] Filed: Apr. 19, 1996

Related U.S. Application Data

[63] Continuation of Ser. No. 439,127, May 11, 1995, abandoned, which is a continuation-in-part of Ser. No. 333,233, Nov. 2, 1994, abandoned, which is a continuation of Ser. No. 152,396, Nov. 12, 1993, abandoned, which is a division of Ser. No. 403,751, Sep. 5, 1989, Pat. No. 5,288,497.

[51] Int. Cl.$^6$ ....................................................... A61K 9/68
[52] U.S. Cl. ........................ 424/440; 424/434; 424/435; 424/484
[58] Field of Search ..................... 424/440, 434, 424/435, 484

[56] References Cited

U.S. PATENT DOCUMENTS

| | | | |
|---|---|---|---|
| 4,311,722 | 1/1982 | Vink et al. | 426/660 |
| 4,389,393 | 6/1983 | Schor et al. | 424/469 |
| 4,452,825 | 6/1984 | Klacik et al. | 426/658 |
| 4,515,769 | 5/1985 | Merritt et al. | 424/49 |
| 4,671,953 | 6/1987 | Stanley et al. | 424/440 |
| 4,749,575 | 6/1988 | Rotman | 424/441 |
| 4,806,356 | 2/1989 | Shaw | 424/440 |
| 4,885,173 | 12/1989 | Stanley et al. | 424/440 |
| 5,004,601 | 4/1991 | Snipes | 514/772.7 |
| 5,035,252 | 7/1991 | Mondre | 132/321 |
| 5,048,544 | 9/1991 | Mascarelli et al. | 131/270 |
| 5,135,752 | 8/1992 | Snipes | 424/435 |
| 5,135,753 | 8/1992 | Baker et al. | 424/435 |
| 5,139,790 | 8/1992 | Snipes | 424/435 |
| 5,176,151 | 1/1993 | Harding | 128/842 |
| 5,244,668 | 9/1993 | Snipes | 424/435 |
| 5,288,497 | 2/1994 | Stanley | 424/440 |
| 5,288,498 | 2/1994 | Stanley | 424/440 |

FOREIGN PATENT DOCUMENTS

| | | |
|---|---|---|
| 644574 | 9/1992 | Australia . |
| 2230439 | 10/1990 | United Kingdom . |
| 2255892 | 11/1992 | United Kingdom . |
| 91/06288 | 5/1991 | WIPO . |
| 91/09599 | 7/1991 | WIPO . |
| 92/10147 | 6/1992 | WIPO . |

*Primary Examiner*—D. Gabrielle Phelan
*Attorney, Agent, or Firm*—Workman, Nydegger & Seeley

[57] ABSTRACT

The present invention relates generally to a cigarette substitute for administering a dose of nicotine. More specifically, the present invention is directed to a nicotine-containing dosage-form comprising a holder member which may be used as part of an effective smoking cessation program or in situations where smoking is undesirable or not permitted. The dosage form is configured as a dosage form having a nicotine-containing composition attached to a holder member. Nicotine is released from the dosage form and absorbed through the intra-oral mucosal surfaces as the nicotine-containing composition releases nicotine within a user's mouth. The holder member facilitates insertion and removal of the dosage form into and out of a user's mouth. The user can selectively insert and remove the dosage form as desired to selectively control the release of nicotine. In addition, the user can insert and remove the dosage form in a manner which meets the user's psychological need or desire for ritualistic oral stimulation similar to cigarette smoking.

17 Claims, 5 Drawing Sheets

Serum Nicotine Concentrations Over Time Depending On The Delivery System

TOBACCO SUBSTITUTE

RELATED APPLICATIONS

This application is a continuation of U.S. patent Ser. No. 08/439,127 filed May 11, 1995, now abandoned, which is a continuation-in-part application of U.S. patent application Ser. No. 08/333,233, filed Nov. 2, 1994, now abandoned, which is a continuation of U.S. patent application Ser. No. 08/152,396, filed Nov. 12, 1993, now abandoned, which is a divisional of U.S. patent application Ser. No. 07/403,751, filed Sep. 5, 1989, now issued as U.S. Pat. No. 5,288,497.

BACKGROUND OF THE INVENTION

1. The Field of the Invention

The present invention relates generally to a tobacco substitute for administering a dose of nicotine. More specifically, the present invention is directed to a nicotine-containing dosage-form having a holder which may be used as part of an effective tobacco cessation program or in situations where smoking is undesirable or not permitted.

2. Background of the Invention

Nicotine is a naturally occurring drug found in tobacco which has both stimulant and depressant effects in the peripheral and central nervous systems (CNS). Nicotine can thus be included in a broad category of CNS-acting drugs. Nicotine occurs as a basic, colorless to pale yellow, very hygroscopic, oily, volatile liquid that has an unpleasant pungent order and a sharp, burning, persistent taste. Nicotine forms salts with almost any acid and therefore exists in a variety of salt forms. Nicotine is considered to be very toxic, and toxic effects develop rapidly following an acute overdose. When nicotine is obtained from tobacco, as by chewing, snuffing or smoking, the amount of nicotine absorbed into the body generally does not build up to a toxic level.

Nicotine can be introduced into the body through many different routes. One of the most popular versions of nicotine use involves the smoking of cigarettes. When the tobacco in a cigarette is ignited, the combustion process causes the release of nicotine vapors. The nicotine in cigarette smoke, suspended on minute particles of "tar" is quickly absorbed through the lung. The absorption of nicotine into the body through cigarette smoke is almost as quick as intravenous administration, with the nicotine reaching the brain within eight seconds after inhalation of the tobacco smoke.

Unfortunately, introducing nicotine into the body in this manner also introduces many other compounds into the body as well. The combustion process of tobacco is complex with about 4,000 compounds being generated during combustion. Among the compounds being generated are those which produce highly undesirable effects such as carbon monoxide, carbon dioxide, nitrogen oxides, ammonia, and many other substances. In addition, many substances are left in the lungs as "tar." The variety of substances generated by burning tobacco include many which are believed to have serious long term health effects. Because of this, in recent years smoking has been increasingly disfavored, and because of second hand inhalation, restrictions have been placed on where an individual may smoke.

Because of these and other undesirable side effects, many attempts have been made to provide acceptable substitutes to cigarettes. Most of these substitutes contain nicotine which is generally considered to be the dependence-producing component in tobacco. Other factors such as social reinforcement, environmental factors (e.g., advertising), and learning behavior may also contribute to tobacco dependence.

Most heavy smokers seem to behave as if they are attempting to adjust the concentration of nicotine within relatively narrow limits. For example, when cigarettes with a relatively high content of nicotine are given to heavy smokers, they tend to reduce the number of cigarettes smoked and alter their inhalation patterns thereby achieving concentrations of nicotine in the blood plasma which are only slightly greater than those to which they are accustomed. Similarly, when heavy smokers are given cigarettes with a very low nicotine content, they change their pattern of inhaling or increase the number of cigarettes smoked in order to avoid declines in plasma nicotine concentrations. This suggests that smokers may be best served by cigarette substitutes which allow for the regulation of plasma nicotine concentrations within specified ranges which mimic cigarettes. Likewise, users of chewing tobacco or other forms of tobacco need a substitute that is capable of mimicking the plasma levels associated with the use of a particular tobacco form.

Cessation of the use of tobacco may be followed by a withdrawal syndrome which varies from person to person in intensity and specific signs and symptoms. Although there is wide variability, the most consistent signs and symptoms are a craving for tobacco, irritability, anxiety, restlessness, and difficulty in concentrating. Drowsiness, headaches, increased appetite, insomnia, and gastrointestinal complaints are also common. The use of nicotine supplements during this withdrawal time has been shown, in some cases, to increase the rate of success for those wishing to quit smoking.

Substitutes currently available include nicotine gum, sublingual lozenges, tablets, nasal sprays, vapor inhalers, and patches. These substitutes rely on the fact that nicotine is readily absorbed through the mucosa and skin. Because nicotine is a strong base, its absorption from the small intestine is limited unless the pH is raised but nicotine is rapidly and extensively metabolized during the first pass through the liver.

The available substitutes, while eliminating the health risks associated with cigarette smoking, do not fully meet the needs of a smoker.

When nicotine gum is used by smokers, they are often encouraged to chew one piece of gum whenever they have the urge to smoke. The instructions generally suggest that the gum should be chewed very slowly until a slight tingling in the mouth is perceived. Once this tingling is felt, it is recommended that the user then stop chewing the gum and wait until this tingling is almost gone (usually within about one minute). This chewing procedure is then repeated periodically for about thirty minutes. This chewing technique is designed to provide constant, slow buccal absorption of nicotine from the gum. By providing slow, constant absorption, nicotine levels in the blood stream can be maintained at a constant level. While there is some evidence indicating that low constant blood levels of nicotine relieves some of the symptoms of nicotine withdrawal, a smoker's craving for tobacco is not mitigated by a relatively low, constant level of nicotine. This is because the nicotine levels derived from smoking are dramatically different in terms of the concentration of nicotine in the blood stream over time from the nicotine levels in the blood stream achieved when nicotine gum is used.

When nicotine is received through smoking, the rapid absorption of the nicotine through the lungs results in an initial peak of nicotine in the blood stream which then subsequently trails off. The blood level peak produced by cigarettes is both higher and sharper than the steadier levels which are obtained from gum or transdermal systems. The initial peak in nicotine concentrations in the blood from smoking is generally between thirty to forty nanograms per milliliter. Furthermore, this peak is attained within about ten minutes. Studies have shown that quick-rise effects are probably necessary for more complete relief from craving in the early stages of cigarette withdrawal. See Russell, M. A. H., In Nicotine Replacement: A Critical Evaluation, Pomerleau, O. F. and Pomerleau, C. S., Eds., Alan R. Liss, Inc., New York, 1988, pp. 63–94. Russell indicates that a rise in the nicotine blood level of at least ten nanograms per milliliter in ten minutes is required to obtain postsynaptic effects at nicotine receptors in the CNS and at autonomic ganglia. These postsynaptic effects may be responsible for the drug-like "high" feelings such as lightheadedness or dizziness experienced by cigarette smokers. Thus, when nicotine can be delivered in a manner which reproduces or mimics the manner in which nicotine is delivered through cigarette smoking, the smoker's craving for cigarettes may be reduced. The slow, constant absorption produced by the intermittent chewing of nicotine gum, fails to achieve this result.

In an effort to mimic the manner in which nicotine is distributed through smoking a cigarette, a user can more aggressively chew the nicotine gum. This, however, is generally not recommended because chewing the gum too rapidly can cause excessive release of nicotine resulting in adverse effects similar to those of excessive smoking such as nausea, hiccups, and irritation of the throat. Chewing nicotine gum aggressively will result in a large amount of nicotine being swallowed because more nicotine is released than can readily be absorbed at the buccal cavity site. If too much nicotine is swallowed, the resultant nausea will most likely cause vomiting. Nicotine gum is thus unable to safely provide a nicotine plasma concentration curve similar to that achieved through smoking cigarettes.

In addition, the use of nicotine gum does not address the psychological needs of the smoker to have something which is placed into the mouth and removed from the mouth in a ritualistic manner. Nicotine gum may also be difficult to tolerate as a long-term treatment. The usefulness of nicotine gum formulations are limited because they taste bad, cannot be used effectively by denture wearers, and may lead to mouth ulcers and heartburn. Furthermore, because of the unique chewing regime which must be imposed to adequately regulate nicotine concentrations in the blood, nicotine gum may be difficult to use in order to regulate nicotine levels within a relatively narrow plasma concentration such as that desired by heavy smokers. Tablet-type smoking substitutes suffer from similar drawbacks.

Transdermal patches which contain nicotine have also been developed. These patches are designed to be placed on one's skin. The nicotine in the patch is then absorbed through the skin. Because of the simplicity of nicotine patches, patient compliance is usually high. Transdermal patches have been developed that can be changed regularly. For instance, patches which are to be changed once a day or, perhaps once a week, are available. Nicotine patches are able to deliver nicotine in such a way that a steady state nicotine concentration can be maintained in the blood plasma. This eliminates the fluctuations that can occur when using gum or tablets which must be taken regularly.

As with the nicotine gum, the delivery of nicotine into the body is at a relatively constant rate. These patches are thus unable to duplicate the plasma nicotine concentration curve obtained through smoking a cigarette. In addition, severe poisoning can result from improper use of these patches. For example, if an individual has a patch applied and then smokes several cigarettes, the plasma nicotine concentration will be much greater than what the individual is used to. This may result in nicotine overdose.

Other considerations must be taken into account when nicotine patches are used. The lethal dose unit for an average adult is about sixty milligrams of nicotine. One cigarette delivers about one milligram of nicotine. Therefore, a patch that is to be effective for twelve or twenty-four hours may contain between thirty and sixty milligrams of nicotine. This presents a safety concern as this represents a potentially lethal dose if nicotine delivery from the patches were significantly increased. This might occur if the patient were to lay on a heating pad or warm water bed. In addition, if the patch is tampered with or ingested by a child, for example, poisoning may occur. Furthermore, nicotine patches do not provide oral stimulation to address the psychological aspects of cigarette craving.

Thus, while current cigarette substitutes are capable of delivering enough nicotine to help alleviate some physical symptoms of nicotine withdrawal, they fail to provide the quick-rise in nicotine blood concentrations which smoking a cigarette provides. They also fail to address the psychological needs of someone who is trying to quit smoking. Many rituals are developed during years of smoking. One such ritual is the periodic placing of something into and out of a person's mouth and the associated oral stimulation of holding a cigarette in one's mouth.

Additionally, patients are usually under-dosed because the physician does not measure baseline nicotine or cotinine levels and does not instruct the patient in the proper use of the gums, tablets and/or patches. This may explain the somewhat low level of success with patches and gum. Some studies indicate that only about twenty percent of those using nicotine patches under prescription managed to quit smoking. Other studies using nicotine gum showed similar results. Nicotine nasal spray also causes problems such as pain or irritation to the nasal mucosa, and while adequate plasma levels of nicotine may be realized, the oral gratification and sensory ritualistic behaviors are left unsatisfied.

BRIEF SUMMARY AND OBJECTS OF THE INVENTION

It is one object of the present invention to provide a nicotine-containing dosage form which can be utilized as part of a long-term smoking cessation program.

Another object of the present invention is to provide a nicotine-containing dosage form which is suitable for use as a smoking substitute whenever smoking is not allowed or desired.

A further object of the present invention is to provide a nicotine-containing dosage form which can maintain nicotine plasma concentrations within a range which alleviates smoking withdrawal symptoms.

A still further object of the present invention is to provide a nicotine-containing dosage form which can provide nicotine plasma concentrations similar to those achieved by smoking a cigarette.

Yet another object of the present invention is to provide a nicotine-containing dosage form which addresses some of the psychological needs of an individual who desires to quit smoking.

A still further object of the present invention is to provide a nicotine-containing dosage form which is suitable for use by those wearing dentures or other dental appliances.

Another object of the present invention is to provide a nicotine-containing dosage form which is easy to use so as to promote patient compliance.

Yet another object of the present invention is to eliminate the craving for a cigarette by allowing the patient to self-dose the amount of nicotine to overcome the person's individual craving.

It is yet another object of the present invention to provide a nicotine-containing dosage form which can be used in conjunction with a patch so that the individual can control the dosage to treat breakthrough cravings as they occur.

It is a still further object of the present invention to provide a nicotine-containing dosage form which allows patients experiencing a relapse to control occasional urges without raising the baseline nicotine plasma concentration levels.

To achieve the foregoing objects, and in accordance with the invention as embodied and broadly described herein, a nicotine-containing dosage form is provided. The dosage form is configured having a nicotine-containing composition attached to a holder member. Nicotine is released from the dosage form and absorbed through the intra-oral mucosal surfaces as the nicotine-containing composition releases nicotine within a user's mouth. The holder member facilitates insertion and removal of the dosage form into and out of a user's mouth. The user can selectively insert and remove the dosage form as desired to selectively control the release of nicotine to satisfy the user's individual craving. In addition, the user can insert and remove the dosage form in a manner which meets the user's psychological need or desire for ritualistic oral stimulation similar to cigarette smoking.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and object of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
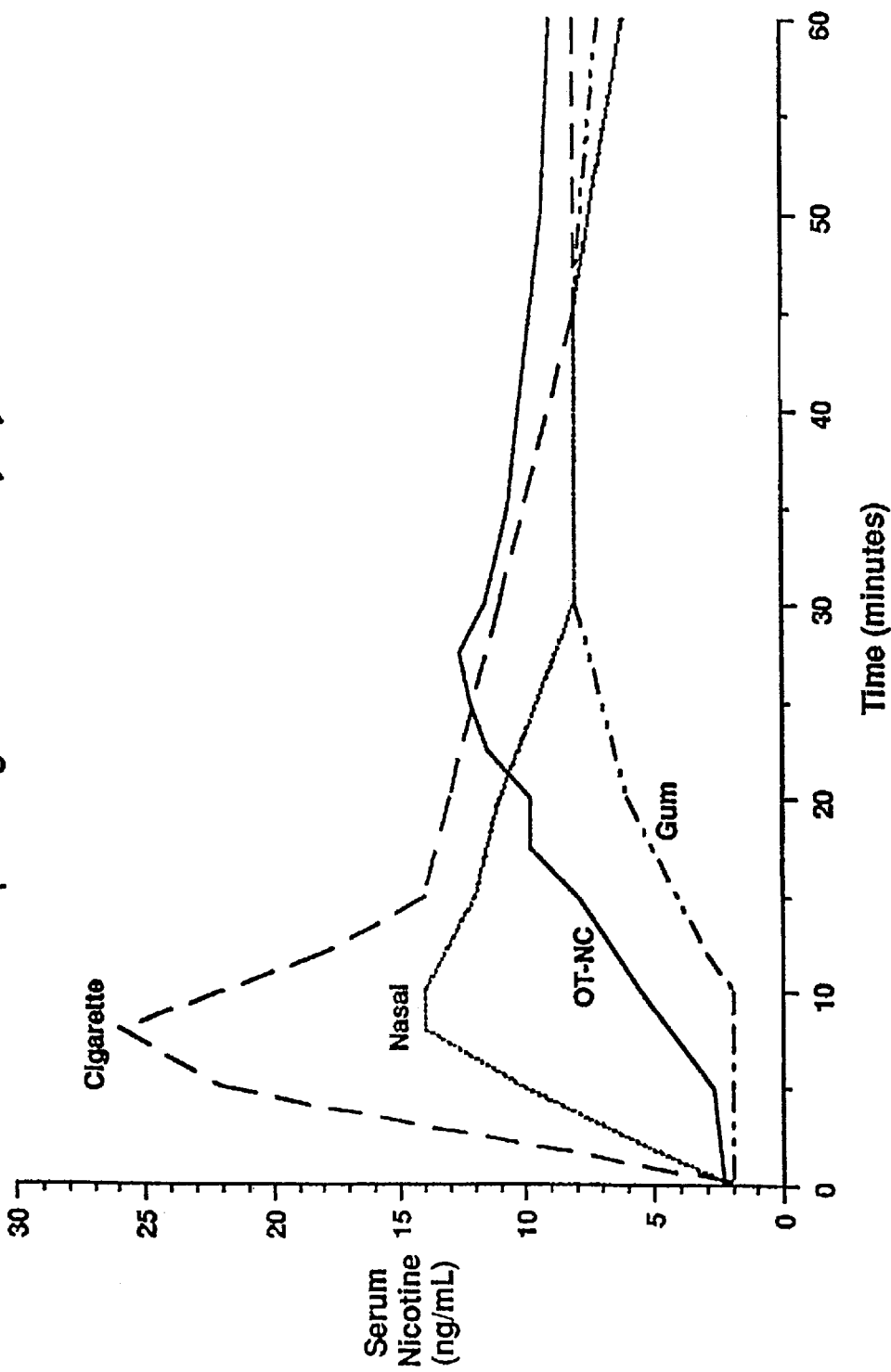
FIG. 1 is a serum nicotine concentration comparison demonstrating the blood plasma level changes in individuals after administration of cigarettes, nasal sprays, gum and the present invention.

The present invention relates to methods of manufacture and compositions which facilitate the transmucosal delivery of nicotine to a patient for use as either a smoking substitute, an aid to smoking cessation, or, as will be discussed later, in the treatment of illnesses such as colitis, Tourette's syndrome, Parkinson's disease, and Alzheimer's disease. Simply stated, the present invention relates to a selectively removable nicotine-containing dosage form permitting transmucosal delivery of nicotine through the mucosal tissues of the mouth, pharynx, and esophagus. The nicotine-containing dosage form of the present invention is capable of delivering nicotine into a patient's blood in a manner which results in attainment of blood nicotine concentrations similar to the blood nicotine concentrations attained through smoking cigarettes to thereby address the physical cravings for nicotine which a smoker develops. In addition, the nicotine-containing dosage form of the present invention provides a patient the opportunity, if desired, for physical manipulation and oral stimulation associated with repeated insertion and removal of the dosage form into and out of the patient's mouth to thereby address some of the psychological cravings which a smoker develops.

The present invention overcomes several of the limitations associated with either nicotine-containing transdermal delivery systems or nicotine-containing gum, tablet, nasal spray, or lozenge delivery systems. One of the primary advantages of the present invention is the ability to selectively vary the amount of nicotine released from the dosage form over time through, for example, patient-controlled behavior such as varying the rate of consumption of the dosage form or removing the dosage form from the mouth and reinserting it, and/or through design adaptations which affect the concentration of absorbable nicotine released from particular portions of the dosage form.

With the nicotine-containing dosage form of the present invention, it is possible to achieve a relatively rapid initial increase in blood nicotine concentration followed by a period of maintenance of a lower blood nicotine concentration and thereby simulate the pattern attained by smoking a cigarette. Thus, the nicotine-containing dosage form of the present invention may provide a more satisfying alternative to smoking than presently available nicotine delivery systems. This ability is demonstrated in FIG. 1 in which the effect of the administration of several popular dosage forms is demonstrated. The initial peak followed by a gradual diminishment of serum nicotine after smoking a cigarette is shown. Although the nasal spray most closely emulates the cigarette line on the graph, nasal sprays do not provide the psychological benefits of an oral dosage form. Of the oral dosage forms tested, the present invention (indicated as OT-NC) has the greatest potential for approximating the physiological and psychological effects of cigarettes. By moderating the speed and intensity of sucking on the dosage form, the serum level can be altered to satisfy an individuals unique craving. Thus, the peak on the graph for the instant invention may be altered to approximate the curve of a cigarette. The transdermal patch information is not included on the chart but requires several hours to reach therapeutic blood nicotine levels and provides a pseudosteady state nicotine concentration.

FIG. 1 also reveals that the administration of conventional nicotine gum results in a slow, gradual increase in serum nicotine that levels out over a prolonged period. Since the administration of gum fails to produce an initial peak, the gum dosage forms fails to emulate the effect of smoking. Similarly, patches produce a slow, gradual increase in serum nicotine that plateaus and stays constant over a prolonged period of time. Like gum, the patches do not produce an initial peak of serum nicotine and thus do not emulate the effect of cigarettes.

One advantage of the present invention is the ability to address the psychological cravings of a cigarette smoker to handle an object which is ritualistically inserted into, held within, and removed from the mouth. The nicotine-containing dosage forms of the present invention comprise a holder member, such as a stick, and a nicotine containing composition attached to the stick. The holder member facilitates selective insertion and removal of the dosage form into and out of a patient's mouth such that a desired physical and psychological effect may be achieved. Unlike nicotine-containing gum, tablets, or lozenges, the dosage form of the present invention can easily be removed to assess the physical effects of the absorbed nicotine, temporarily cease the absorption of nicotine, or to inspect the size and condition of the dosage form at any time. In addition, the holder member prevents inadvertent swallowing of the dosage form and facilitates positioning of the dosage form in a comfortable and adjustable fashion within the oral cavity. Thus, local mucosal irritation from continued contact with nicotine-containing gum, lozenges, or tablets may be avoided by using the holder member to re-position the dosage form within the oral cavity as desired.

The present invention may be used as a smoking substitute by a person in a situation where smoking is either not permitted or not desirable. In this situation, the nicotine-containing dosage form of the present invention provides a satisfying alternative to smoking a cigarette by permitting both physical and psychological simulation of the smoking experience. The present invention may also be used by persons who desire to stop smoking but experience difficulties due to the physical dependence on nicotine and the psychological dependence on the rituals of smoking which have been developed. Such persons must go through a withdrawal period during which the smoking habit is gradually overcome. In this situation, the nicotine-containing dosage form of the present invention provides a means to satisfy both the physical and psychological cravings and, hopefully, permit the person to resist the craving to smoke cigarettes during a withdrawal period sufficient to free the person from the smoking habit.

Figure 2:
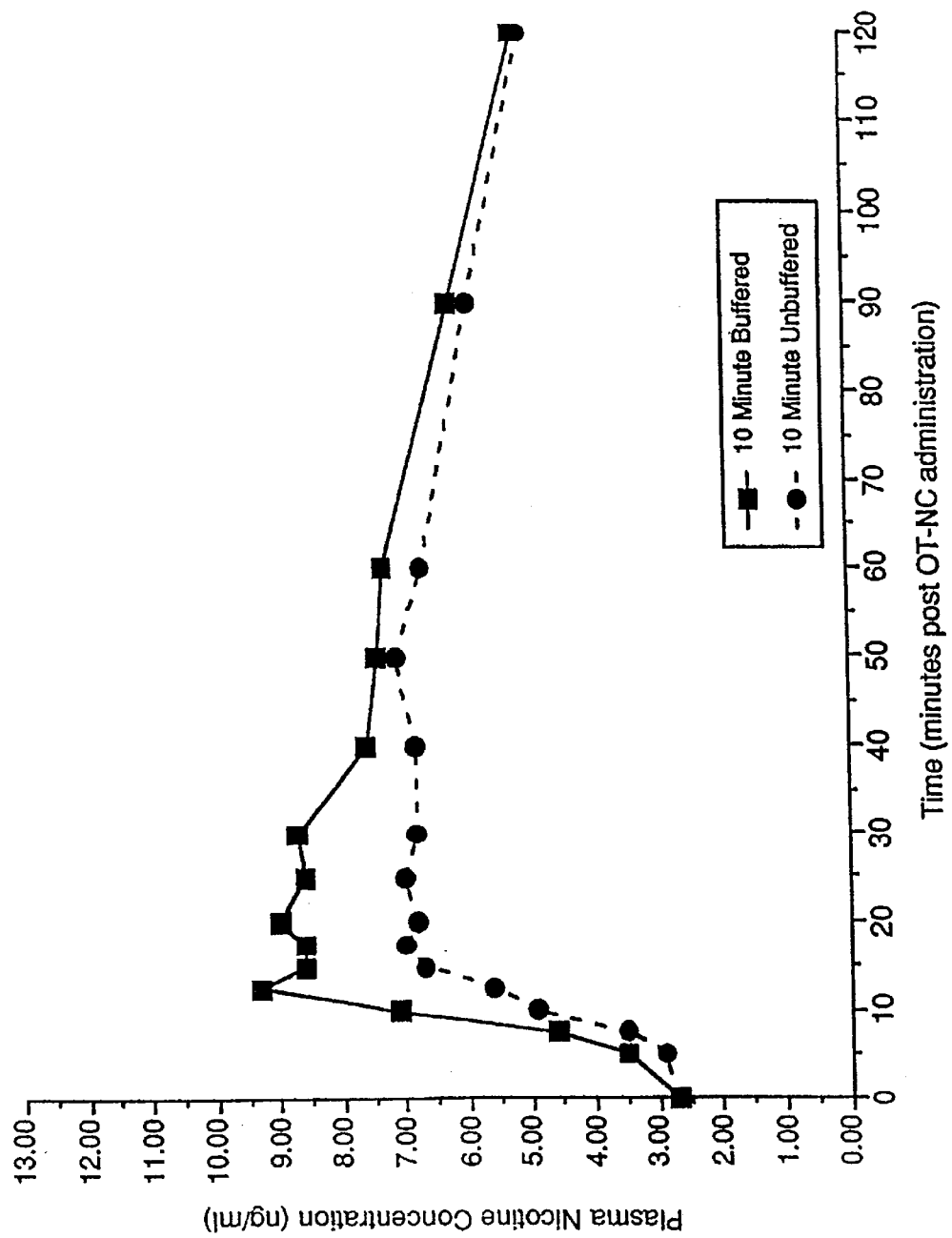
FIG. 2 is a comparison graph demonstrating buffered versus unbuffered absorption rates.

Nicotine is available in the present invention in either a free base or salt form. Nicotine base is readily absorbed through mucosal membranes but is highly volatile. Nicotine salts, on the other hand, are not readily absorbable through mucosal membranes but are much more stable. Nicotine is also available as an ionic complex in the form of a polyacrylic cation exchange resin. Pharmaceutically acceptable nicotine salts include, but are not limited to nicotine hydrochloride, nicotine dihydrochloride, nicotine sulfate, nicotine monotartrate, nicotine bitartrate, nicotine citrate, nicotine zinc chloride monohydrate and nicotine salicylate. In an alkaline environment, i.e., pH above about 7, and in the presence of an aqueous medium, such as saliva within the oral cavity, nicotine salts react to form nicotine base. Because saliva normally has a somewhat neutral pH, the incorporation of an alkaline salt into the dosage-form of the present invention will buffer the pH and facilitate the reaction to form readily absorbable nicotine base. Preferred alkaline salts include sodium carbonate, sodium bicarbonate, potassium carbonate, potassium bicarbonate, trisodium phosphate, disodium hydrogen phosphate, sodium oxylate, sodium succinate, sodium citrate, trimethamine and sodium salicylate. Buffering may also affect stability. The results of buffering are graphically demonstrated in FIG. 2.

In addition to nicotine in a releasable form which is readily absorbed transmucosally, the nicotine-containing compositions in accord with the present invention may contain other ingredients such as flavorings, sweeteners, flavor enhancers, lubricants, binders and fillers. With respect to flavorings, it should be noted that it is desirable to discourage nicotine use by young people. Accordingly, it may be desirable to flavor the nicotine-containing composition in a manner which is unattractive to young people. It may even be desired to provide an unflavored nicotine-containing composition which would be palatable to smokers accustomed to the taste of nicotine yet unattractive to others not so accustomed.

The nicotine-containing dosage form of the present invention consists of any nicotine-containing composition capable of delivering readily absorbable nicotine to the intra-oral mucosal tissues in combination with an attached holder member. The nicotine form that is incorporated into the nicotine-containing composition may be pure nicotine or any compound thereof. The method of manufacture may be any suitable method known in the art including, but not limited to, the addition of a form of nicotine to a dissolvable or non-dissolvable matrix buccal dosage form intended to be sucked or passively dissolved in the mouth. The method of attachment of the holder member similarly may be any suitable method known in the art including, but not limited to, positioning of the holder member within a non-solidified nicotine-containing composition which is subsequently solidified by compression, injection molding or other means, and attachment by gluing, as with confectioner's glue, or bonding by other means, to the pre-manufactured nicotine-containing composition.

One method in accord with the present invention comprises mixing the desired ingredients to form a powdered compressible matrix material which is compressed into an integral solid mass under high pressure. This process is referred to as "powder compaction." During compression, the mass is attached to a holder member to form a nicotine-containing dosage form. Alternatively, the mass may be attached to a holder member in another manner, such as by gluing with confectioner's glue.

More specifically, each of the components including compressive carbohydrate fillers and binders, is mixed with the other components in dry form to produce the compositions of the present invention. It is presently preferred to use the method of geometric dilution in adding the various components together prior to the mixing process.

Other components that are typically used in powder compaction include ingredients such as flavorings, sweeteners, flavor enhancers, releasing agents, and buffers. It is preferred that these ingredients be provided in a powder form to facilitate mixing even if the ingredients happen to be insoluble or otherwise chemically incompatible.

Once complete mixing is accomplished, the mixture is compressed under relatively high forces to provide a coherent dosage form. Compressive forces in the range of from approximately 100 Newtons to approximately 150 Newtons are presently preferred, however, any force which is sufficient to compress the ingredients into a coherent, integrated mass could be used. As a result, the compressed mass is held together by physical, rather than chemical means.

The extent of the compressive force can be modified to vary the dissolution rate, i.e., the rate at which the composition dissolves within the oral cavity. In particular, the greater the compressive force used, the slower the dissolution rate will be. The dissolution rate may also be affected chemically with other ingredients. For example, the dissolution rate may be decreased by adding hydrophobic agents such as calcium stearate or the dissolution rate can be increased with the addition of hydrophilic agents.

When employing the present invention, there is no need to heat the mixture to a molten mass as has been the practice in the past in forming drug-containing confections. As a result, the present method avoids the use of high temperatures which volatilizes nicotine and also avoids undesired chemical reactions which may occur between the various ingredients in a heated or liquid environment. Nevertheless, good mixing and uniform product are provided.

The confectionery mass may be attached to a holder such as a stick or other similar type of holder. The holder may be glued to the confection by confectioner's glue or other food grade glues. Alternatively, the holder may be compressed into the dosage form by the compressive forces described above.

One method of creating an embodiment of the present invention utilizes a mold block with an anterior having a cavity formed in any desired shape so that the ingredients described above can be compressed sufficiently to form an appropriately shaped dosage. Each half of the mold block can be removed in order to remove the confection once it is sufficiently compressed. A ram is used to compress the cavity. Following compression of the confection, the stick is securely bound in place.

The stick may take various shapes. For example, it may be desirable for the stick to be oval or triangular in cross section.

Another method utilized to produce an embodiment of the present invention involves a nondissolvable matrix into which the nicotine is placed.

The nicotine may be incorporated into a variety of possible nondissolvable containment matrixes. For example, the nicotine may be incorporated into a sponge-like matrix; the nicotine may be microencapsulated; the nicotine may be held within a microsponge; the nicotine may be contained within a permeable membrane or screen-like barrier; or the nicotine may be held within other nondissolvable containment vehicles capable of releasing the nicotine for transmucosal administration.

The scope of the present invention includes embodiments having a permeable membrane or screen-like barrier which retains the nicotine containing vehicle.

The barrier may be screen-like with relatively large pores or membrane-like with relatively small pores. The barrier preferably has a pore size sufficient to permit the nicotine to pass therethrough. It is important that the nicotine be retained within the barrier under conditions outside the patient's mouth and that the nicotine be capable of permeating the barrier within the patient's mouth.

For example, in one preferred embodiment within the scope of the present invention, the medicament medium viscosity is sufficiently high outside the mouth such that the surface tension at the barrier pores prevents the nicotine from permeating the barrier. But once the dosage-form is placed within the patient's mouth, the viscosity of the medicament medium is lowered so that the nicotine permeates the barrier. In one embodiment the viscosity of the medicament medium is lower within the mouth due to saliva contact with the medicament medium. In other embodiments the viscosity of the medicament medium is lower within the mouth due to an increased temperature within the mouth.

In another embodiment within the scope of the present invention, the nicotine within the medicament medium permeates the barrier in response to pressure effects within the mouth. For instance, negative pressure caused by sucking the dosage-form draws the medicament through the barrier. Alternatively, positive pressure caused by squeezing the dosage-form forces the medicament through the barrier.

One embodiment utilizes microencapsulated drug particles retained within a permeable barrier. Microencapsulated drugs are nicotine particles or droplets which have been coated with a protective coating material. Typical coating materials include fats, waxes, triglycerides, fatty acids, fatty alcohols, ethoxylated fatty acids and alcohols, stearates, sugars, poly(ethylene glycol), certain metals, gums, hydrocolloids, latexes, and various polymer-based formulations such as polyethylene, ethyl cellulose, ethylene-vinyl acetate, ethylene-acrylic acid, polyamides, and some enteric polymers.

The protective coating material of microencapsulated nicotine prevents nicotine degradation by moisture, retards oxidation of the nicotine, decreases evaporation and sublimation, protects the nicotine from reaction with other ingredients, and masks unpleasant taste of nicotine. Nicotine microencapsulation techniques are known in the art.

Another embodiment utilizes a plurality of drug-containing sponge-like matrixes which are retained within the barrier. Sponge-like matrixes, which include microsponges, are devices capable of entrapping a medicament and then releasing the medicament over time. These sponge-like matrixes are biologically inert, non-irritating, non-mutagenic, non-allergenic, non-toxic, and non-biodegradable. They can even improve medicament stability. Suitable microsponges or sponge-like matrixes are known in the art.

Like true sponges, the sponge-like matrixes or microsponges contain a myriad of interconnecting voids within a non-collapsible structure with a large porous surface. The size of the sponge-like matrix as well as the number and size of the internal pore structure can be varied depending on the medicament size and viscosity.

The medicament is released from a sponge-like matrix in response to a suitable "trigger". For example, rubbing or pressing the sponge-like matrix, elevating the temperature of the matrix (as within the patient's mouth vis-a-vis ambient temperature), or introducing suitable solvent such as saliva can cause a controlled release of the medicament. Pressure may also be used to release the drug from the sponge-like matrixes. Squeezing and sucking a dosage-form containing the sponge-like matrixes saturated with the medicament will release the medicament.

In other embodiments within the scope of the present invention, the sponge-like matrix or microencapsulated nicotine particles may be held together with a biocompatible binding material or adhesive (either dissolvable or nondissolvable) such as sodium carboxymethylcellulose, sodium alginate, and tragacanth.

In yet another embodiment of the present invention, the sponge-like matrix or microencapsulated nicotine particles may be retained within a compressed powder dosage-form or other dissolvable using the previous discussed powder compaction process.

In these embodiments, a plurality of microencapsulated nicotine particles are compressed together in a dosage-form with compressible sugar and other ingredients as previously described. A handle is also preferably attached to the dosage-form.

The handle or holder may be attached to the nondissolvable matrix by incorporating the holder into the nondissolvable matrix as the dosage-form is being formed.

Alternatively, the holder may be glued, compressed, screwed, snapped, or otherwise attached to the nondissolvable matrix once the matrix is formed. In yet other embodiments, dosage-forms may be assembled immediately prior to uses by sliding nondissolvable connectable dosage elements containing a suitable medicament onto an appropriately configured holder. Optionally dissolvable or nondissolvable flavored connectable elements may also be slid onto the holder.

Figure 3:
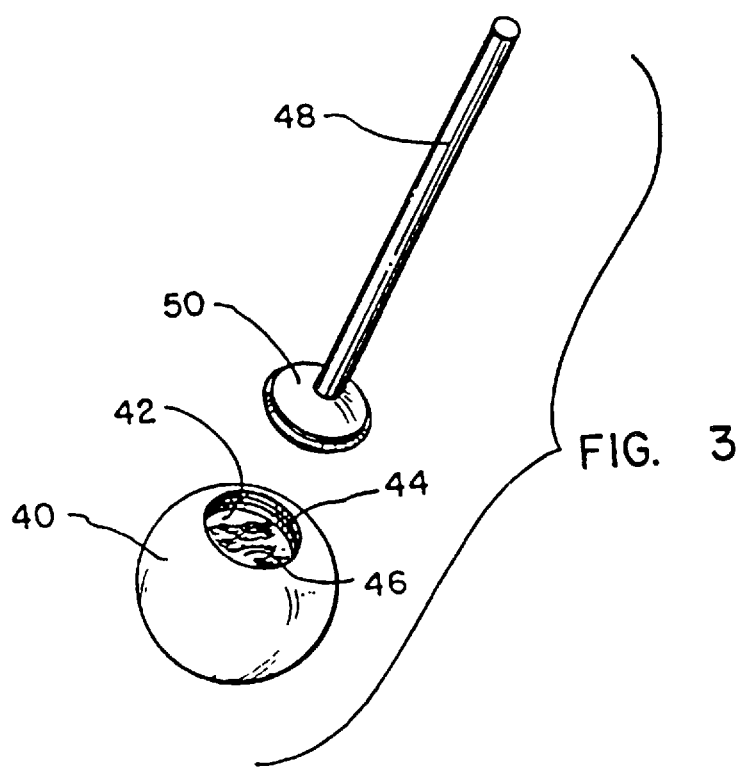
FIG. 3 illustrates a nondissolvable dosage form.

In one embodiment illustrated in FIG. 3, a permeable barrier 40 defines a chamber 42 and an opening 44 to the chamber. The chamber is filled with a nicotine composition 46 in the form of microsponges, microencapsulated drug particles, a medicament medium, or other similar drug-containing formulation. A holder 48 includes a cover 50 for opening 44. Cover 50 is configured to securely seal opening 44 while at the same time provide means for attaching holder 48 to the dosage-form. In this way, the quantity and concentration of nicotine may be placed within the dosage-form prior to use. The nicotine may even be replenished or replaced during use if necessary.

It will be appreciated that attachment of the nicotine-containing matrix onto a holder can facilitate the transmucosal absorption of a variety of therapeutic agents. Attachment to a holder also facilitates verifiable transfer of the medication of the patient. For instance the medication may be bound to a dye such that loss of color indicates transfer of the medication to the patient. The holder permits the nicotine-containment matrix to be positioned at the desired location within the patient's mouth and provides a convenient point of reference enabling the medical professional to verify the proper placement of the matrix.

Figure 4:
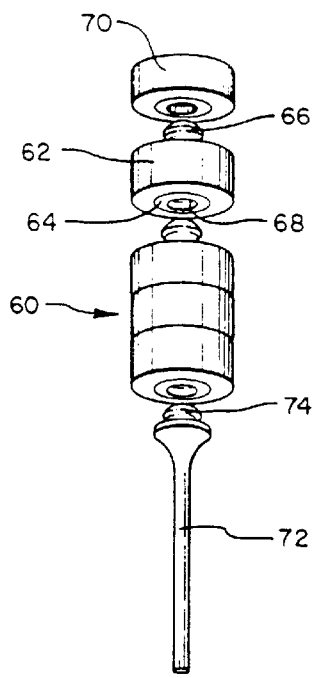
FIG. 4 illustrates a dissolvable dosage form having wafers of varying concentrations of nicotine.

Dosage-form 60, illustrated in FIG. 4, contains a plurality of connectable dosage elements 62. Dosage elements 62 include a solid core 64 defining a male coupling 66 and a female coupling 68. A dosage cap 70 is configured substantially the same as dosage elements 62, except that the solid core does not define a male coupling. The dosage elements are preferably constructed of a screen-like material such as woven fabric or a perforated sheet of material which is molded or fabricated around the solid core. The solid core may be constructed of a suitable biocompatible material such as polyethylene. The screen-like material defines a chamber for holding the desired medicament and releases the medicament in substantially the same manner as described above in connection with FIGS. 1A–1C.

Dosage-form 60 is constructed by interlocking a plurality of dosage elements through their respective male and female couplings. A holder 72 which includes a male coupling 74 constructed at one end thereof is preferably coupled to the connectable dosage elements. The ability to assemble a dosage-form prior to use permits the dosage-form to be "customized" to the individual patient or circumstances. Various concentrations of a drug, or even multiple drugs may be administered in this manner.

Figure 5:
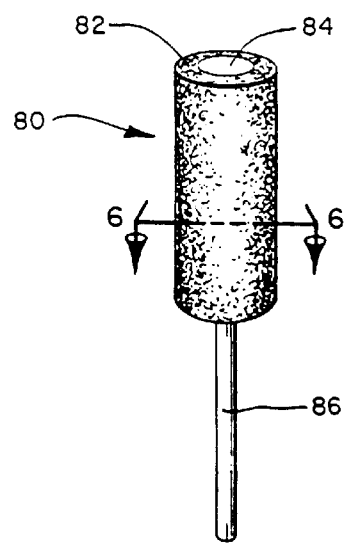
FIGS. 5–9 illustrate nondissolvable dosage forms capable of administering variable quantities and concentrations of nicotine.
Figure 6:
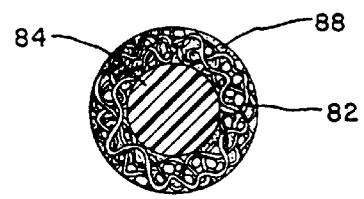

FIGS. 5 and 6 illustrate another possible dosage-form embodiment within the scope of the present invention. Dosage-form 80 includes a covering material 82 molded around a semisolid core 84. The semisolid core is preferably mounted to a holder 86. Covering material 82 is preferably a thick mesh or perforated sheet having the desired medicament 88 embedded therein which will permit the medicament to leach out or otherwise enter the patient's mucosal membrane. The medicament may be powdered, liquid, microencapsulated, or otherwise trapped in the covering material 82 so that the medicament will be released within the oral environment.

Figure 7:
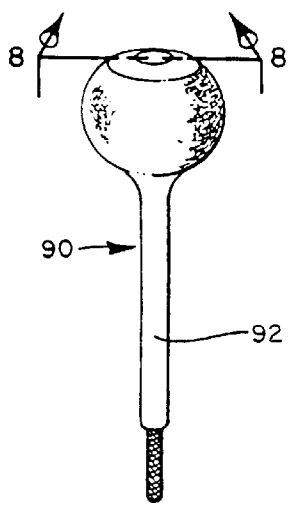
Figure 8:
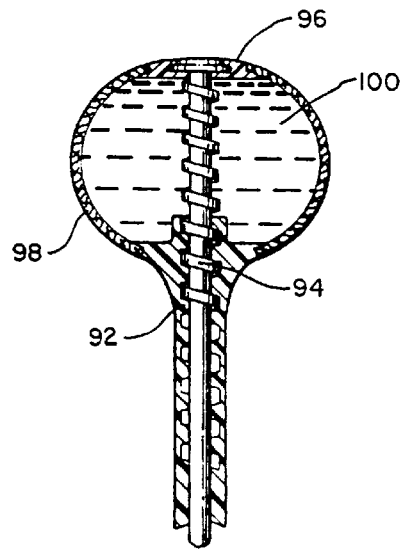
Figure 9:
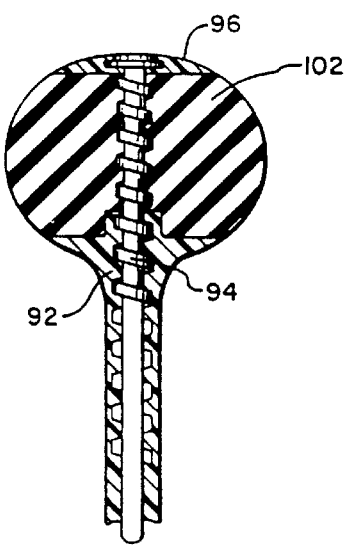

The embodiments illustrated in FIGS. 7–9 permit the nicotine administration rate to be controlled by adjusting the pressure applied to a medicament medium. Dosage-form 90 shown in FIGS. 7 and 8 includes a holder 92 and a screw 94 internally threaded within holder 92. Secured to holder 92 and to screw cap 96 is a semipermeable membrane 98 which provides a containment barrier for a quantity of medicament medium 100. Membrane 98 is similar to those described above by having pore size sufficient to permit medicament to pass therethrough within an oral environment. The medicament medium may be a liquid medicament solution or a suspension.

In operation, dosage-form 90 is placed within the patient's mouth and screw 94 is twisted such that medicament medium 100 is placed under pressure thereby increasing the rate the medicament permeates membrane 98.

The embodiment illustrated in FIG. 9 is similar to that shown in FIGS. 7 and 8 except that the medicament is embedded within a semisolid medicament medium 102 embedded with medicament which is capable of being compressed. In operation, the dosage-form is placed within the patient's mouth and screw 94 is twisted such that medicament medium 102 is compressed thereby directly releasing the medicament for absorption across the patient's mucosal membrane.

Figure 10:
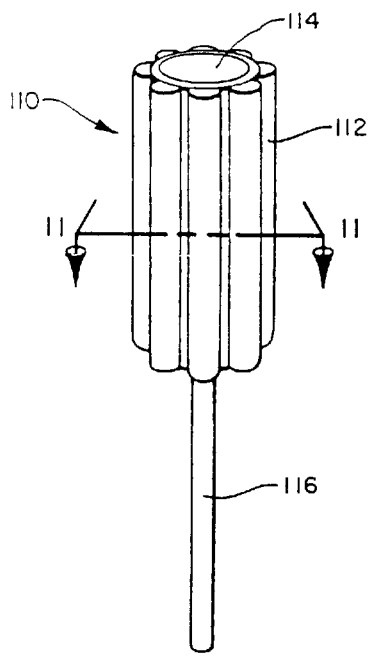
FIGS. 10–15 illustrate a series of dissolvable dosage forms for administering the nicotine in varying concentrations, some of which are formed of compressed powder.
Figure 11:
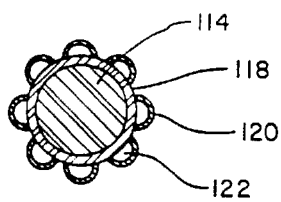

FIGS. 10 and 11 show yet another possible embodiment within the scope of the present invention. Dosage-form 110 includes a plurality of tube-like members 112 located around the periphery of a semisolid core 114. The semisolid core is preferably mounted to a holder 116. A layer of expandable material 118 may optionally be located between the tube-like members and the semi-solid core.

The tube-like members are formed from a screen-like material 120, such as nylon or dacron mesh, which is molded in a semicylindrical shape. The tube-like members are mounted to expandable material 118 such that the screen-like material provides a barrier for a quantity of medicament 122. Expandable material 118 is preferably constructed of methylcellulose or similar material encased in a porous mesh which will hydrate and expand when placed in the patient's mouth. Upon expansion increased pressure is exerted on the porous tube-like members, thereby increasing the rate medicament is released form the dosage-form.

Figure 12:
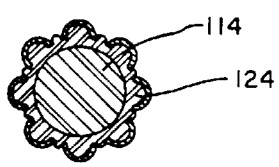

The embodiment illustrated in FIG. 12 is similar to that shown in FIGS. 10 and 11, except that the medicament is embedded directly within an expandable material 124 such as methylcellulose. The medicament is released as material 124 expands within the patient's mouth.

Another optional embodiment which is not shown in the figures replaces semisolid core 114 with a hollow tube constructed of polyethylene or similar material which can be injected with air such that it expands against the tube-like members containing the medicament. The pressure (from a know volume of injected air) and the pore size covering the tube-like members governs the delivery rate of the medicament.

Figures 13, 14:
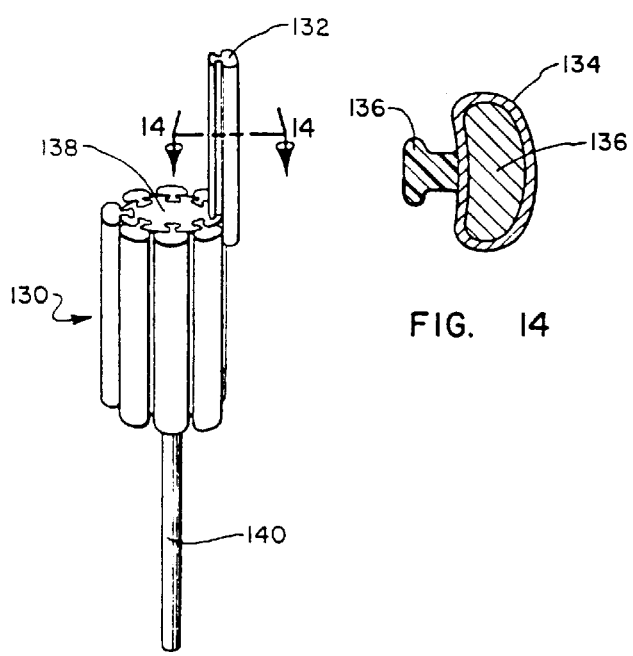

FIGS. 13 and 14 show a dosage-form which is a variation of the embodiment illustrated in FIG. 10. Dosage-form 130 of FIGS. 13 and 14 includes a plurality of tube-like members 132. Tube-like members 132 are shown in cross-section in FIG. 14. Members 132 include a screen-like material 132 which encapsulates a quantity of medicament medium 136.

A rigid stem 138 is attached to screen-like material 134 and is configured to be slid and locked into corresponding slots formed in a solid core 138. A handle 140 is preferably secured to the solid core to facilitate placement and removal of the dosage-form.

Dosage-form 130 may be assembled prior to use by sliding the rigid stems of a plurality of tube-like members 132 into corresponding slots formed in the solid core. The ability to assemble a dosage-form prior to use permits the dosage-form to be "customized" to the individual patient or circumstances. Various concentrations of nicotine, or even multiple drugs may be administered in this manner.

Figure 15:
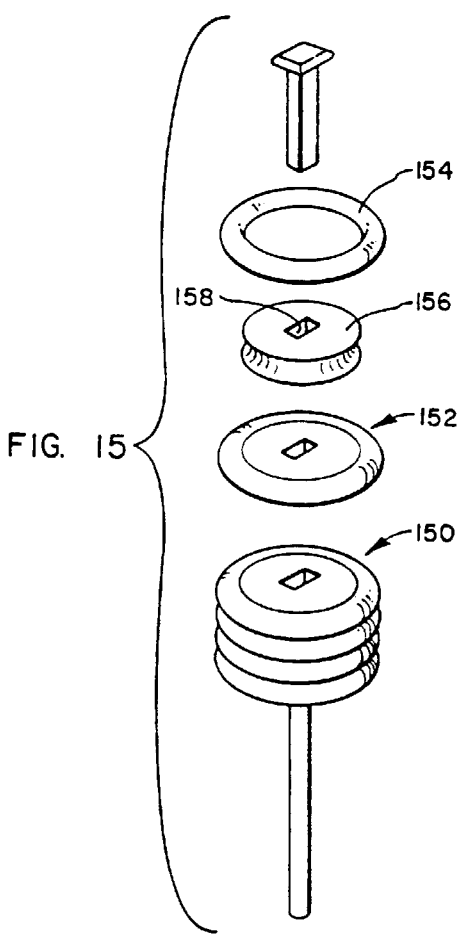

FIG. 15 illustrates another possible dosage-form embodiment which may be individually assembled prior to use. Dosage-form 150 of FIG. 15 is assembled from a plurality of dosage elements 152. Each dosage element includes a ring 154 which is positioned around a semi-solid disk 156. Rings 154 are fabricated from appropriate porous material such as woven nylon or dacron or sheets of perforated nylon, polypropylene, or polyethylene. Rings 154 are filled with medicament, either liquid or powder. The semisolid disks define a hole 158 therein such that a plurality of dosage elements may be assembled on a holder. The ability to assemble a dosage-form 150 prior to use permits the dosage-form to be "customized" to the individual patient or circumstances. Various concentrations of nicotine, or even multiple drugs, may be administered in this manner.

The foregoing dosage-forms are given to illustrate various embodiments which may be made in accordance with the present invention. It is to be understood that the foregoing dosage-form configurations are not comprehensive or exhaustive of the many types of embodiments of the present invention. It is important that the nondissolvable dosage-form configuration be biocompatible and capable of releasing the nicotine for absorption through the patient's mucosal tissues. The configuration should preferably have a structure, shape, and texture which is palatable to the patient.

Placing a nicotine dosage-form onto a holder also facilitates the temporary removal of medication for inspection or the reduction of the effect when necessary. Unlike administration of nicotine orally or even sublingually, the present composition can easily be removed to assess the effect induced at any particular time. When a pill or lozenge is used, removal from the patient's mouth at an intermediate stage to assess effect is generally impractical, if not impossible.

In contrast to a lozenge the nondissolvable drug-containment matrixes attached to a holder can also prevent or make much more difficult the aspiration of the dosage-form. One major problem with existing lozenges and the like is their tendency to crumble. Once the lozenge disintegrates, controlled transmucosal delivery is less ideal and the particles are swallowed. Many of the dosage forms set forth herein dissolve but do not or cannot disintegrate.

In addition, either or both the drug and the permeation enhancer may be dispersed uniformly throughout the dissolvable solid matrix composition or may be selectively dispersed, i.e., stratified or coated, to thereby vary the absorption of the drug from selected portions of the dissolvable solid matrix. It will be appreciated that a stratified nicotine-containing composition could be formulated to effect an initial relatively rapid rise in blood nicotine concentration followed by maintenance of a relatively lower blood nicotine concentration. This may be accomplished, for example, by formulating a two-layer composite matrix comprising an inner matrix and an outer matrix. The solubility of the matrices could be different such that the outer matrix is more rapidly dissolved within the oral cavity than the inner matrix.

Alternatively, or in addition, the concentration of nicotine compound within the matrices could be different such that the outer matrix releases a higher quantity of nicotine than the inner matrix. In any of these multilayer embodiments, the blood nicotine concentration will rise relatively more rapidly while the patient consumes the outer matrix than while the patient consumes the inner matrix.

Additional selectivity and control of nicotine release and absorption rates could be obtained with more matrix layers and/or combinations of the above-described methods, i.e., varying the matrix dissolvability, varying the permeation enhancement, or varying the drug concentration throughout the matrices. It will be appreciated that more than two layers could also be incorporated into the multilayer nicotine-containing composition to further vary the effect as desired. The presence of additional layers can be indicated by color or flavor changes.

In the formulations disclosed, the amount of nicotine in each dosage form is preferably less than 30 mg., and most preferably between 0.5 to 20.0 mg. to avoid accidental overdosage by swallowing. The presently preferred embodiment utilizes nicotine bitartrate. Although the dosage form of the present invention comprises a holder member which prevents swallowing of the dosage form, it may nevertheless be preferable to keep the nicotine dose in individual dosage forms low to thereby allow a patient to easily selectively control the amount of nicotine ingested by controlling the number of dosage forms used.

As disclosed in the above-referenced patent, the nicotine-containing compositions intended to be sucked are preferably buffered to increase and maintain the percentage of unionized drug to facilitate transport and absorption through the oral mucosa and thereby aid in transmucosal absorption. A preferred formulation is at a pH of 6.8–11. As described above, buffered formulations will include sodium carbonate, sodium phosphate, calcium carbonate, magnesium hydroxide, trimethamine and other substances known in the art.

The addition of a buffer can result in a decrease in the stability. Alternatively, the buffer can be encapsulated in a water soluble material to improve stability but still provide the optimal pH in the mouth as the unit dissolves.

The buffered nicotine-containing compositions formulated by direct compression may comprise a mixture of directly compressible excipients, a pharmaceutically acceptable salt of nicotine and a base sufficient to maintain a specified pH level within the patient's mouth. The preparation is mixed with suitable diluents and compressed or compressed with a granulated "core" comprising a portion of the buffering base ingredient.

Another method involves cold compression, extrusion, or drying of a mixture containing an inert filler material, an inert binder material, and a solution of nicotine or nicotine-containing substance dissolved in alcohol to formulate a nicotine-containing dosage form. This form may include a coating which can, for example, comprise a substance to enhance dissolvability of the composition or a substance to act as local anesthetic and thereby decrease the perceived local irritation from a nicotine absorption site. It will be appreciated that a method similar to the "coating" method could also be used to provide a multi-layer nicotine-containing composition wherein the layers permit nicotine to be released in different amounts or absorbed at different rates similar to the approach discussed above with respect to "stratified" dissolvable solid matrices.

Another embodiment of the present invention utilizes a compressed carbohydrate powder matrix, but has mixed substantially uniformly therein a coated buffering agent. The buffering agent is coated with a water soluble material so that the buffering agent is released in the mouth of the patient. Upon release, the buffering agent will modify the pH of the saliva in the mouth of the patient to enhance absorption of the nicotine. By coating the buffering agent prior to mixing with the matrix, stability of the combined matrix is maintained.

In addition, methods for formulating dissolvable nicotine-containing matrices for buccal dosage forms, which melt in the user's oral cavity but are stable in higher shipment and storage temperatures are known and can be incorporated.

As discussed previously, tobacco substitutes have several uses. A smoker who does not wish to expose others to the effects of second-hand smoke may use a tobacco substitute for short periods, such as when traveling on an airplane, or during working hours.

Long-term tobacco users may have incurred damage from chewing tobacco or from cigarettes so that they may no longer use those products, yet still feel the need for nicotine.

For those who wish to cease smoking or using snuff, tobacco substitutes may be used to wean the individual from the nicotine craving. By slowly reducing the amount of nicotine consumed, the individual may reduce the craving without experiencing significant withdrawal side effects.

A similar group of tobacco substitute users utilize the substitute only to deal with peak periods of craving. These individuals do not regularly use the substitute, but instead use it only occasionally when needed to deal with occasional cravings beyond their resolve.

It will be appreciated that although nicotine is often consumed in cigarette form with the accompanying deleterious effects of tar and smoke, nicotine has been found to have beneficial effects such as treatment of Alzheimer's disease, ulcerative colitis, Tourette's syndrome, and Parkinson's disease. Although presented as a tobacco substitute, the present invention is also directed to the beneficial administration of nicotine for treatment of these and other ailments. In these applications, the handle of the present invention allows the patient to titrate the amount of nicotine to prevent side effects such as nausea, etc. The present dosage form not only aids in the comfort of the patient by preventing side effects, but also provides an added measure of safety as the dosage form may be removed not only by the patient, but also by a care provider. Unlike other dosage forms with slower or delayed absorption rates, the user may remove the present dosage form at the first signs of nausea and need not consume the entire dosage form. This opportunity is not available with ingested therapies or with slower acting dosage forms such as patches.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A selectively removable nicotine-containing dosage form for use in the transmucosal delivery of nicotine to a patient, the dosage form comprising:

(a) a powdered compressed carbohydrate matrix dissolvable in the oral cavity of a patient;

(b) a pharmacologically effective dose of nicotine dispersed in the matrix such that when the matrix dissolves in the mouth of the patient, the pharmacologically effective dose of nicotine is released for absorption through the mucosal tissue of the mouth, pharynx, and esophagus of the patient;

(c) a buffering agent to modify the saliva pH in the mouth of the patient; and (d) a holder member secured to the matrix, said holder member being so configured as to facilitate manipulation of the nicotine-containing dosage form in and to permit the selective removal and insertion of the dosage form into and out of the patient's mouth.

2. A selectively removable nicotine-containing dosage form as recited in claim 1, wherein the dose of nicotine free base equivalents is within the range of about 0.1 mg to 30 mg.

3. A selectively removable nicotine-containing dosage form as recited in claim 1, wherein the nicotine is present within the matrix in the form of nicotine free base.

4. A selectively removable nicotine-containing dosage form as recited in claim 1, wherein the nicotine is present within the matrix in the form of a nicotine salt.

5. A selectively removable nicotine-containing dosage form as recited in claim 4 further comprising a buffering agent dispersed into the matrix, said buffering agent being capable of increasing the pH within the oral cavity and thereby increasing the unionized portion of the drug for improved absorption through the oral mucosa.

6. A selectively removable nicotine-containing dosage form as recited in claim 1, wherein the matrix further comprises multiple layers of compositions.

7. A selectively removable nicotine-containing dosage form as recited in claim 6, wherein the multiple layers contain different quantities of nicotine.

8. A selectively removable nicotine-containing dosage form as recited in claim 1, further comprising a coating layer containing an absorption enhancing agent.

9. A selectively removable nicotine-containing dosage form as recited in claim 1, further comprising an outer coating layer containing nicotine.

10. A selectively removable nicotine-containing dosage form as recited in claim 1, wherein the nicotine is dispersed into the matrix so that the concentration of nicotine available for absorption through the mucosal tissues of the mouth, pharynx, and esophagus varies over time as the matrix is dissolved in the mouth of the patient.

11. A selectively removable nicotine-containing dosage form as recited in claim 6, wherein the concentration of nicotine within an outer layer of the matrix is greater than the concentration of nicotine within an inner layer of the matrix.

12. A method for producing a selectively removable nicotine-containing dosage form for use in transmucosal delivery of nicotine to a patient, said method comprising the steps of:

(a) obtaining a pharmacologically effective dose of nicotine;

(b) dispersing said nicotine within a mixture of powdered compressed carbohydrate matrix material, said matrix material capable of dissolving within the mouth of a patient;

(c) forming said matrix material and nicotine into a solid integral mass;

(d) securing a holder member to said solid integral mass.

13. A selectively removable nicotine-containing dosage form for use in the transmucosal delivery of nicotine to a patient, the dosage form comprising:

(a) a soluble, powdered compressed carbohydrate matrix;

(b) nicotine disbursed within the carbohydrate material, the nicotine being capable of absorption through mucosal tissues of the mouth, pharynx, and esophagus and being disbursed substantially uniformly throughout the carbohydrate material at a temperature below the melting point of the nicotine and the carbohydrate material and compressed with the carbohydrate material into a solid integral mass which is capable of dissolving in the mouth of the patient so that the nicotine is released for absorption through mucosal tissues of the mouth, pharynx, and esophagus upon dissolution of the integral mouth mass in the mouth of the patient;

(c) a microencapsulated buffering agent which is also disbursed substantially uniformly throughout the integral mass, the buffer being capable of modifying and maintaining the pH in the mouth such that a majority of the drug remains non-ionized in order to facilitate transmucosal absorption of the drug; and (d) a holder secured to the integral mass so as to form a nicotine-containing dosage form, the holder means being configured so as to permit convenient insertion and removal of the nicotine-containing integral mass into and out of the mouth of the patient.

14. A selectively removable nicotine-containing dosage form as recited in claim 13, wherein the microencapsulation is water soluble so as to dissolve in the mouth of the patient.

15. A selectively removable nicotine-containing dosage form as recited in claim 13, wherein the buffering agent is encapsulated in a water soluble material.

16. A selectively removable nicotine-containing dosage form as recited in claim 13, wherein the nicotine is in the form of a nicotine salt.

17. A selectively removable nicotine-containing dosage form as recited in claim 13, wherein the nicotine is in a free base form.

* * * * *